(12) United States Patent
Bernard et al.

(10) Patent No.: US 6,325,808 B1
(45) Date of Patent: Dec. 4, 2001

(54) ROBOTIC SYSTEM, DOCKING STATION, AND SURGICAL TOOL FOR COLLABORATIVE CONTROL IN MINIMALLY INVASIVE SURGERY

(75) Inventors: Christopher J. Bernard; Hyosig Kang, both of Troy; Barton L. Sachs, Delmar; Sunil K. Singh, Slingerlands; John T. Wen, Niskayuna, all of NY (US)

(73) Assignee: Advanced Realtime Control Systems, Inc., Stephentown, NY (US)

( * ) Notice: Subject to any disclaimer, the term of this patent is extended or adjusted under 35 U.S.C. 154(b) by 0 days.

(21) Appl. No.: 09/208,264

(22) Filed: Dec. 8, 1998

(51) Int. Cl.$^7$ ............... A61B 17/04; B25J 9/18; G05B 19/19
(52) U.S. Cl. ............... 606/139; 606/170; 318/568.11; 700/245; 700/264; 901/1
(58) Field of Search .................... 606/170, 130, 606/139, 145, 1; 600/104–107, 114, 118; 414/730, 5, 2; 318/568.11; 700/245, 264; 901/1

(56) References Cited

U.S. PATENT DOCUMENTS

| | | | |
|---|---|---|---|
| 3,821,498 | 6/1974 | Schaefer, Jr. et al. | 200/18 |
| 3,916,701 | 11/1975 | Butler | 74/57 |
| 4,628,765 | 12/1986 | Dien et al. | 74/665 A |
| 4,781,519 | * 11/1988 | Monforte | 414/730 |
| 4,982,725 | 1/1991 | Hibino et al. | 128/4 |
| 5,078,140 | * 1/1992 | Kwoh | 606/130 |
| 5,086,400 | 2/1992 | Hayati et al. | 395/95 |
| 5,101,681 | 4/1992 | Shpigel | 74/479 |
| 5,184,601 | 2/1993 | Putman | 128/4 |
| 5,195,388 | 3/1993 | Zona et al. | 74/479 |
| 5,219,351 | 6/1993 | Teubner et al. | 606/130 |
| 5,231,693 | 7/1993 | Backes et al. | 395/99 |
| 5,311,868 | 5/1994 | Carbini et al. | 128/653.5 |
| 5,336,982 | 8/1994 | Backes | 318/568.22 |
| 5,368,015 | 11/1994 | Wilk | 128/4 |
| 5,417,210 | 5/1995 | Funda et al. | 128/653.1 |
| 5,476,357 | 12/1995 | Arai | 414/729 |

(List continued on next page.)

FOREIGN PATENT DOCUMENTS

WO 90/11167   10/1990   (WO).
WO 93/13916    7/1993   (WO).

OTHER PUBLICATIONS

Faraz et al., "A Robotic Case Study: Optimal Design For Laparoscopic Positioning Stands," Experimental Robotics Laboratory (ERL), School of Engineering Science, Simon Fraser University, Burnaby, British Columbia, Canada V5A 1S6, p. 1–8. Apr. 1997.

(List continued on next page.)

Primary Examiner—Gary Jackson
(74) Attorney, Agent, or Firm—Heslin Rothenberg Farley & Mesiti P.C.

(57) ABSTRACT

A robotic system for minimally invasive surgery includes a surgical tool and a docking station for restraining movement of the surgical tool to four degrees of freedom about an incision point in a patient. The docking station includes a plurality of actuators for moving the surgical tool relative to the incision in the patient, and a controller operably connected to the actuators so that movement of the surgical tool may be collaboratively controllable both actively by the controller and manually by a surgeon. Desirably, the surgical tool and the docking station are releasably attachable together. Also disclosed is a computer implemented method employing a first docking station attachable to a suturing surgical tool and a second docking station attachable to gripping surgical tool for autonomously tying a knot in suturing.

32 Claims, 17 Drawing Sheets

U.S. PATENT DOCUMENTS

| | | | |
|---|---|---|---|
| 5,503,617 | 4/1996 | Jako | 600/201 |
| 5,518,163 | 5/1996 | Hooven | 227/5 |
| 5,524,180 * | 6/1996 | Wang et al. | 600/118 |
| 5,553,198 | 9/1996 | Wang et al. | 395/80 |
| 5,572,999 | 11/1996 | Funda et al. | 128/653.1 |
| 5,610,488 | 3/1997 | Miyazawa | 318/568.11 |
| 5,624,398 | 4/1997 | Smith et al. | 604/95 |
| 5,630,431 | 5/1997 | Taylor | 128/897 |
| 5,631,973 | 5/1997 | Green | 382/128 |
| 5,662,587 | 9/1997 | Grundfest et al. | 600/114 |
| 5,702,407 | 12/1997 | Kaji | 606/139 |
| 5,728,113 | 3/1998 | Sherts | 606/145 |
| 5,740,699 | 4/1998 | Ballantyne et al. | 74/490.06 |
| 5,748,767 | 5/1998 | Raab | 382/128 |
| 5,749,879 | 5/1998 | Middleman et al. | 606/139 |
| 5,754,741 | 5/1998 | Wang et al. | 395/86 |
| 5,762,458 | 6/1998 | Wang et al. | 414/1 |
| 5,776,126 | 7/1998 | Wilk et al. | 606/1 |
| 5,792,165 | 8/1998 | Klieman et al. | 606/170 |
| 5,797,900 | 8/1998 | Madhani et al. | 606/1 |
| 5,813,978 | 9/1998 | Jako | 600/201 |
| 5,820,623 * | 10/1998 | Ng | 606/130 |
| 5,823,993 * | 10/1998 | Lemelson | 604/51 |

OTHER PUBLICATIONS

Cao et al., "Task and Motion Analyses in Endoscopic Surgery," 1996 ASME IMECE Conference Proceedings; 5th Annual Symposium on Haptic Interfaces for Virtual Environment and Teleoperator Systems, Atlanta, Georgia, p. 583–590 (1996).

Funda et al., "Optimal Motion Control for Teleoperated Surgical Robots," SPIE vol. 2057, p. 211–222 (Apr. 1993).

Cohn et al., "Millirobotics for Telesurgery," Proceedings of the First International Symposium on Medical Robotics and Computer Assisted Surgery, Pittsburgh, PA, Sep. 1994.

* cited by examiner

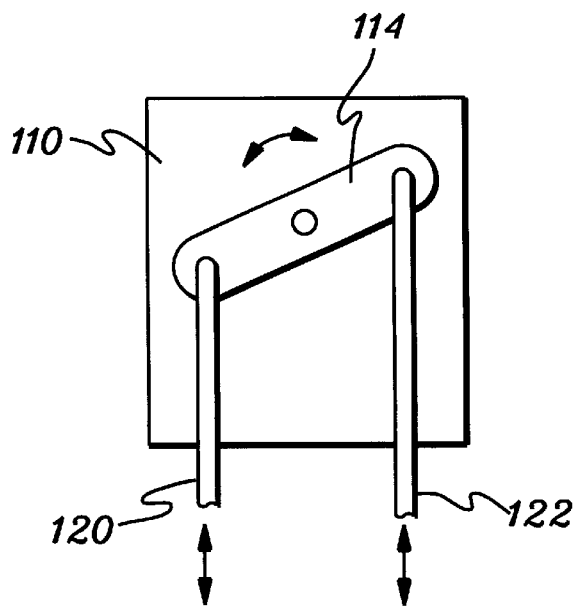
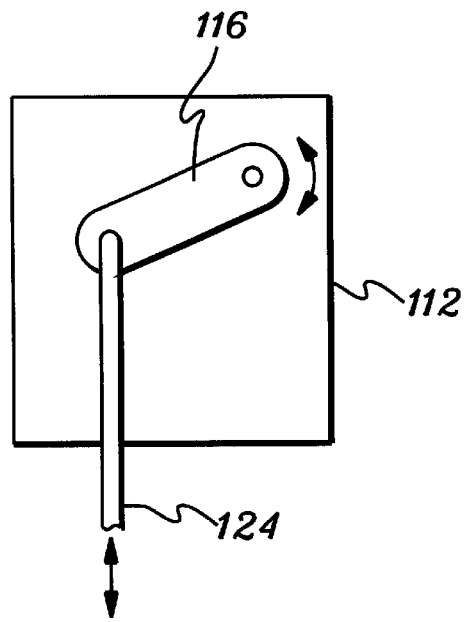
fig. 7    fig. 8
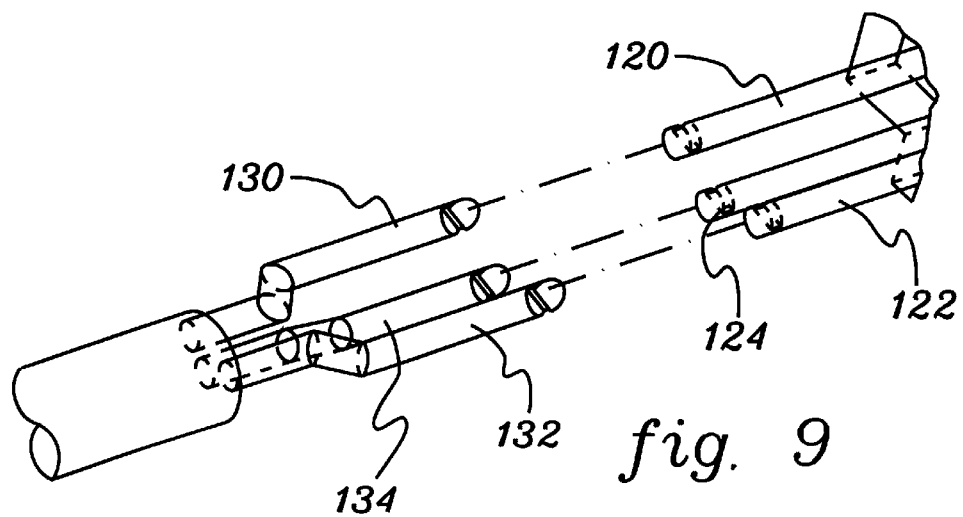
fig. 9

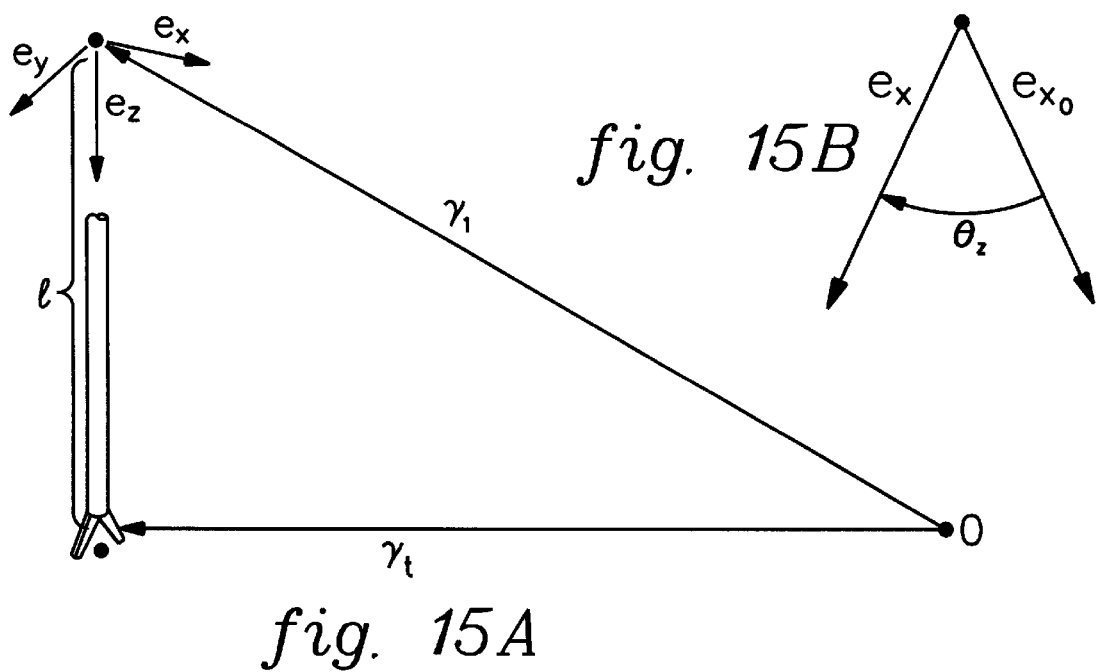
*fig. 15B*
*fig. 15A*
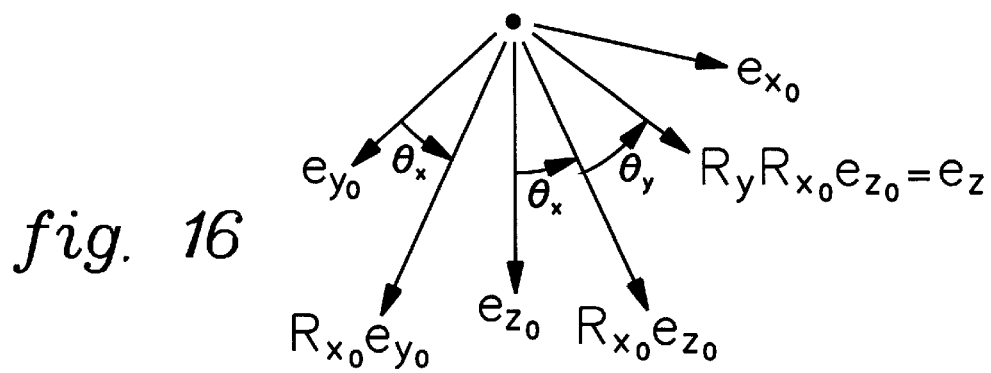
*fig. 16*
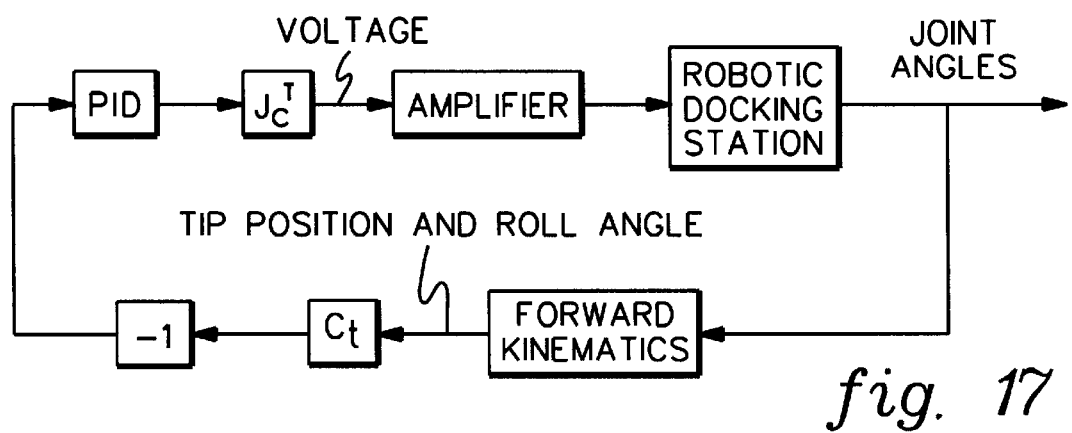
*fig. 17*

ROBOTIC SYSTEM, DOCKING STATION, AND SURGICAL TOOL FOR COLLABORATIVE CONTROL IN MINIMALLY INVASIVE SURGERY

FIELD OF THE INVENTION

The present invention relates generally to minimally invasive surgery, and more particularly, to a system for minimally invasive surgery having a docking station and one or more surgical tools which are releasably and interchangeably attachable to the docking system, and in which the docking station and the surgical tools are collaboratively controllable both manually by a surgeon and actively by a computer.

BACKGROUND INFORMATION

Open surgery traditionally involves operative procedures in which one or more large incisions are made in a patient. The incision and the dissection required for access and visualization by the surgeon during the operative procedure contributes to increased pain to and delayed recovery of the patient.

Minimally invasive surgery is a cost-effective alternate to open surgery whereby the operative procedures are performed using specialized surgical instruments designed to fit into the body through one or more small incisions. The surgeon monitors the operative procedure on a display via an endoscopic camera inserted through one of the small incisions. By eliminating large incisions and extensive dissections, the pain to the patient and the time for recovery is reduced.

Surgical instruments for assisting a surgeon in minimally invasive surgery typically have an elongated body with a handle at one end and an end effector such as a grasper or scissors at the other end. The surgeon inserts the end effector through a small incision in the patient and manipulates the instrument by pivoting it about the incision, rotating it about the incision, sliding it through the incision, and actuating the end effector.

Teleoperated systems have been employed in which a pair of surgical instruments are coupled to a pair of robotic arms. The robotic arms are coupled via a controller to a pair of master handles. The master handles can be moved and actuated by the surgeon to produce a corresponding movement of the surgical instrument and actuation of the end effector.

Compared to open surgery, minimally invasive surgery is affected by physical, visual, motor, spatial, and haptic constraints. As a result of these constraints, there is an extended learning curve that surgeons must go through to gain the required skill and dexterity. Furthermore, there is a great deal of variability even among trained surgeons. Time motion studies of minimally invasive surgeries indicate that for operations such as tissue dissection, suturing, knot tying, and suture cutting, the operation time variation between surgeons can be as large as fifty percent. In suturing, it is noted that the major difference between surgeons lies in the proficiency of the surgeon at grasping a needle and moving the needle to a desired position and orientation without slipping or dropping the needle.

A drawback with use of the above-noted surgical instruments and teleoperated systems for minimally invasive surgery is that a high level of dexterity is required to accurately control the position of the surgical instrument and actuate the end effector. Another drawback is that the handles and end effector have a master-slave relationship so that movement of the handles causes a corresponding movement of the end effector. Still another drawback is that minimally invasive surgery requires usage of a variety of different surgical instruments during an operative procedure which requires the surgeon to switch between different surgical instruments and position each surgical instrument in the patient before continuing the operative procedure.

Therefore, there exists a need for a compact system for minimally invasive surgery in which the system includes one or more docking stations for controlling the position of one or more releasably attachable surgical tools and in which the docking station and an end effector of the surgical tool are manually controllable solely by a surgeon, collaboratively controllable by both the surgeon and computer, or autonomously controllable by a computer, e.g., in tying a knot in suturing.

SUMMARY OF THE INVENTION

The above-mentioned needs are met by the present invention which relates in one aspect to a docking system for use with a surgical tool in minimally invasive surgery in which the surgical tool has a handle, an end effector and is operable by a surgeon for actuating the end effector. The docking station includes a first support attachable to a stand and positionable adjacent to an incision in a patient. Means attachable to the first support are provided for restraining movement of the surgical tool through the incision to four degrees of freedom, and means are provided for releasably attaching the surgical tool to the restraining means.

Desirably, the restraining means comprises means for pivoting the surgical tool about an incision in a patient, means for rotating the surgical tool about an axis through the incision, and means for translating the surgical tool into and out of the incision. The restraining means may further comprises a plurality of actuators for pivotal, rotational, translational movement of the surgical tool, and a controller for controlling the actuators. Advantageously, the restraining means is collaboratively controllable actively by a controller and manually by a surgeon.

Another aspect of the present invention relates to a surgical tool for minimally invasive surgery in which the surgical tool includes an elongated body having a first end and a second end, an end effector attached to the first end of the elongated body, a handle attached to the second end, and means for releasably attaching the handle to a docking station operable to restrain movement of the surgical tool to four degrees of freedom.

Desirably, the second end of the elongated body is releasably attachable to the handle and the elongated body and the end effector are disposable. The handle may include a plurality of actuators operably connected to the end effector for actuating the end effector. Advantageously, the handle includes means for translating at least one rod, and preferably three rods, through the elongated body for actuating the end effector.

Another aspect of the present invention relates to a system for minimally invasive surgery in which the system includes a surgical tool and a docking station for restraining movement of the surgical tool to four degrees of freedom about an incision in a patient. The docking station includes a plurality of actuators for moving the surgical tool relative to the incision in the patient, a controller operably connected to the actuators, and wherein movement of the surgical tool is collaboratively controllable by the controller and a surgeon.

Still another aspect of the present invention relates to a method for forming a knot in a suture thread inserted through an entry point on a first portion to be sutured and exited through an exit point on a second portion to be sutured in which one end of the suture thread is attached to a needle and the needle is attached to a first jaw of a suturing end effector of a suturing surgical tool and the tail of the suture thread is attached to the gripping end effector of a gripping surgical tool. The method includes the steps of contacting a second jaw of the suturing end effector to an elongated body of the gripping surgical tool, rotating the suturing surgical tool until the suture thread drapes over the second jaw, moving the suturing end effector so that the elongated body of the gripping tool is disposed between the jaws of the suturing end effector, passing the needle from the first jaw to the second jaw, and moving the suturing end effector away from the gripping end effector to form a knot in the suture thread.

The method may also include the step of repeating the steps to form a square knot. Desirably, the method further includes the step of computer implementing control of the suturing surgical tool and the gripping surgical gripping tool to autonomously perform the steps of contacting, rotating, passing, and retracting.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be readily understood from the following detailed description of preferred embodiments taken in conjunction with the accompanying drawings in which:

FIG. 7 is an enlarged view taken along line 7—7 in FIG. 6;

FIG. 8 is an enlarged view taken along line 8—8 in FIG. 6;

FIG. 9 is an enlarged perspective view of the releasably attachable rods of the suturing surgical tool shown in FIG. 6;

FIGS. 15A and 15B are vector diagrams illustrating a collaborative control process;

FIG. 16 is a vector diagram illustrating an alternative collaborative control process;

FIG. 17 is a block diagram for collaborative control of the system shown in FIG. 1;

DETAILED DESCRIPTION THE PREFERRED EMBODIMENTS

Figure 1:
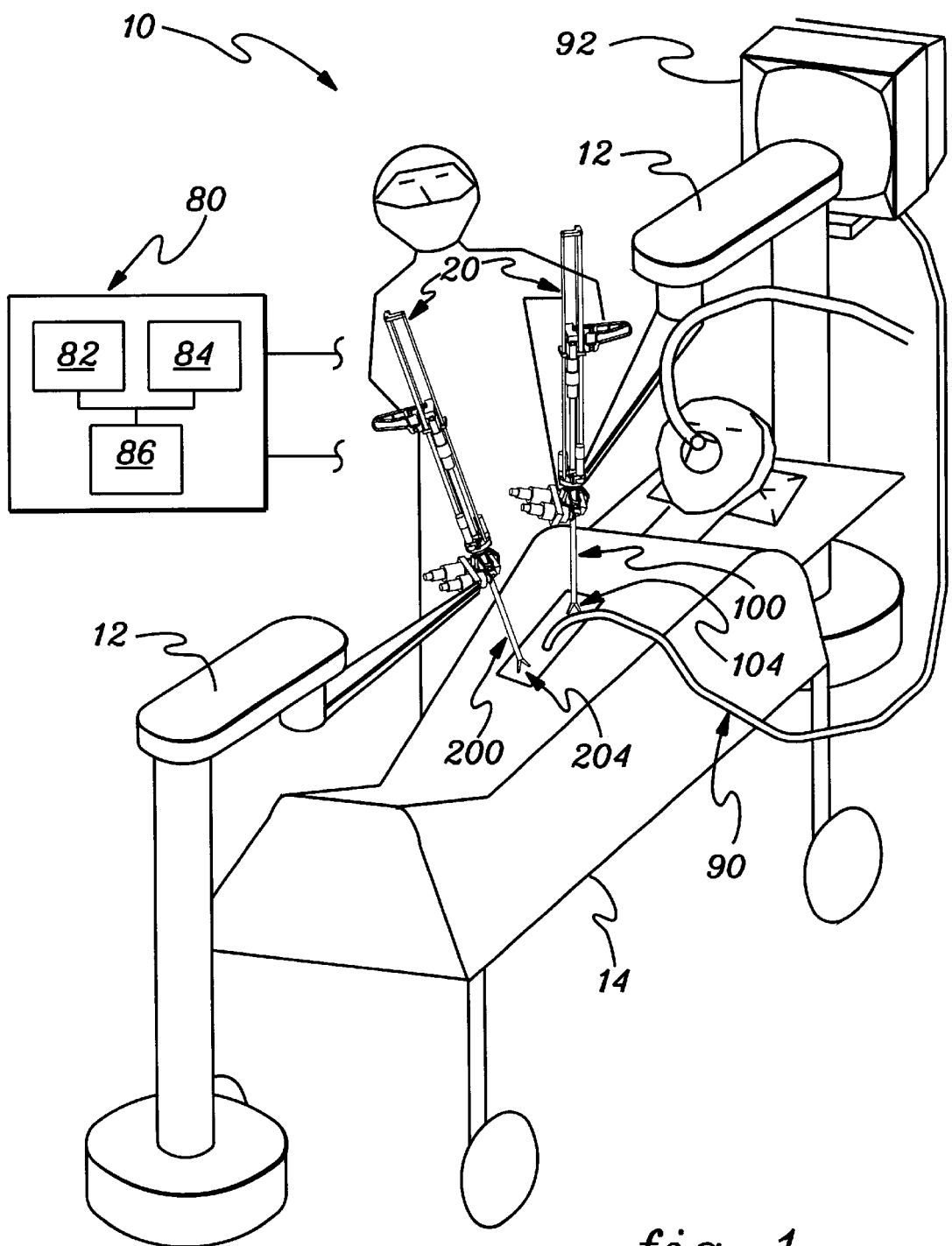
FIG. 1 is a perspective view of one embodiment of a system for minimally invasive surgery according to the present invention.

FIG. 1 illustrates one embodiment of a system 10 according to the present invention for minimally invasive surgery such as laparoscopic surgery. In this exemplary embodiment, system 10includes two docking stations 20, each of which is supported by a stand 12. One of docking stations 20is releasably attached to a suturing surgical tool 100and the other docking station 20 is releasably attached to a gripping surgical tool 200. Docking stations 20 and surgical tools 100 and 200 are operatively connected a controller 80, e. g., a microprocessor or a computer, for autonomous control by controller 80 or collaborative control manually by surgeon and actively by controller 80 as explained in greater detail below.

In this illustrated embodiment, a patient is typically positioned on an operating table 14. For laparoscopic surgery, surgical tools 100 and 200 are inserted into respective incisions in the abdomen of the patient. An endoscope 90 may also be inserted into the patient through a third incision. Endoscope 90 is operably connected to a monitor 92 for displaying images of the internal organs of the patient.

Figure 2:
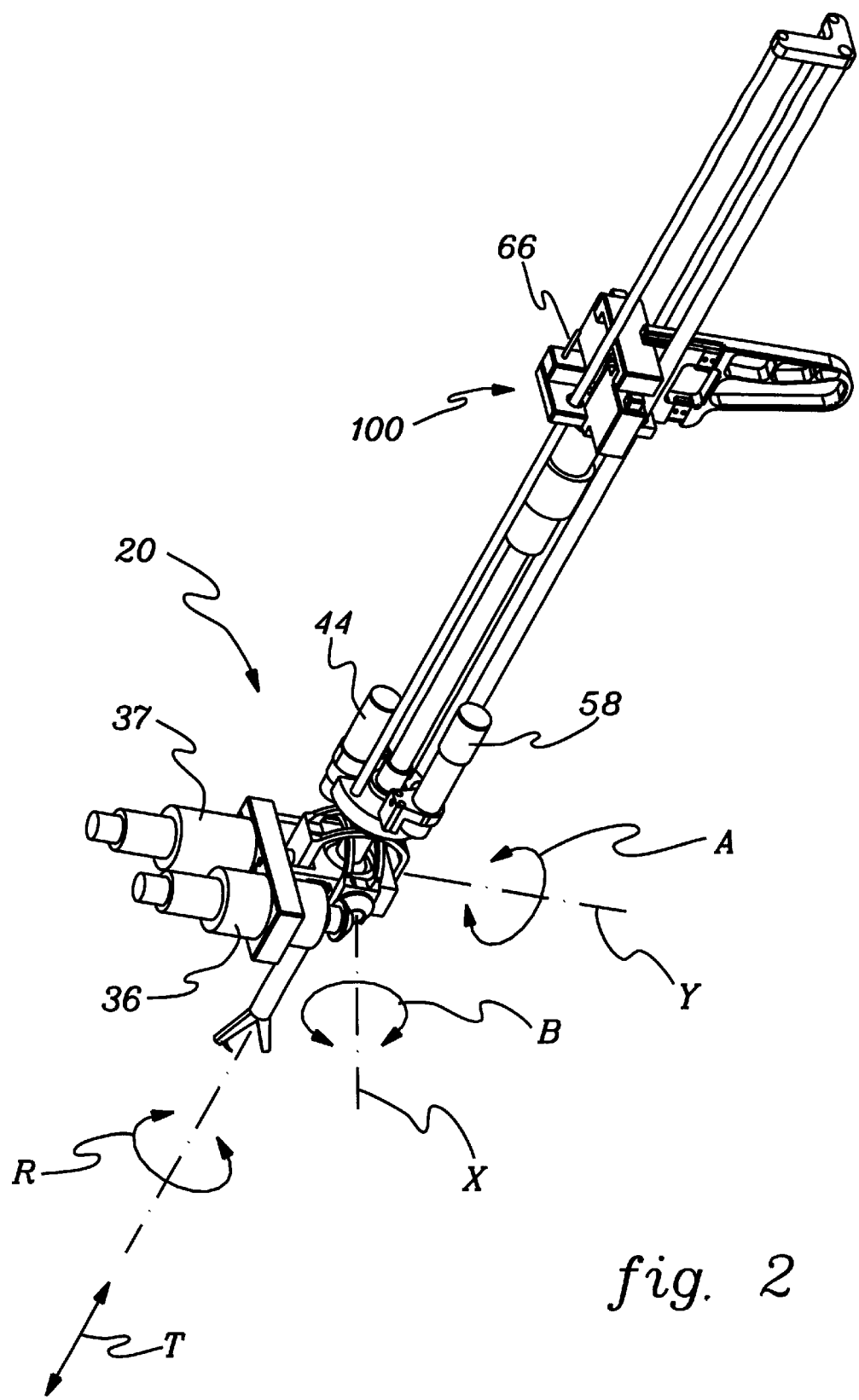
FIG. 2 is an enlarged perspective view of one of the docking stations and the suturing surgical tool shown in FIG. 1.

Each docking station 20 is operable to manually or actively selectively position or orientate surgical tools 100 and/or 200, and in particular, position and orientate an end effector 104 and/or 204 such as a suturing end effector or a gripping end effector. As shown in FIG. 2, docking station 20 desirably constrains, limits, guides and/or controls movement of surgical tool 100 to four degrees of freedom about an incision in the patient. For example, docking station 20 provides pivotal movement of surgical tool 100 in the direction of double-headed curved arrows A and B, rotational movement of surgical tool 100 in the direction of double-headed curved arrow R, and translational movement of surgical tool 100 in the direction of double-headed arrow T.

Figure 4:
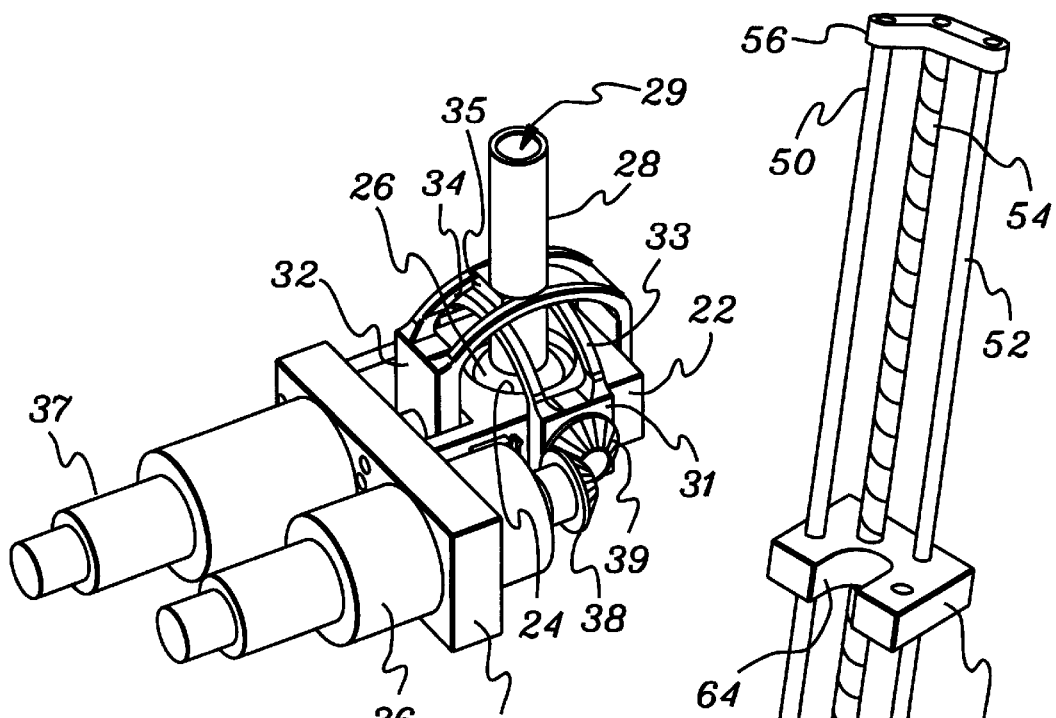
FIG. 4 is an enlarged perspective view of a portion of the docking station, shown in FIG. 3, for pivoting a surgical tool.
Figure 3:
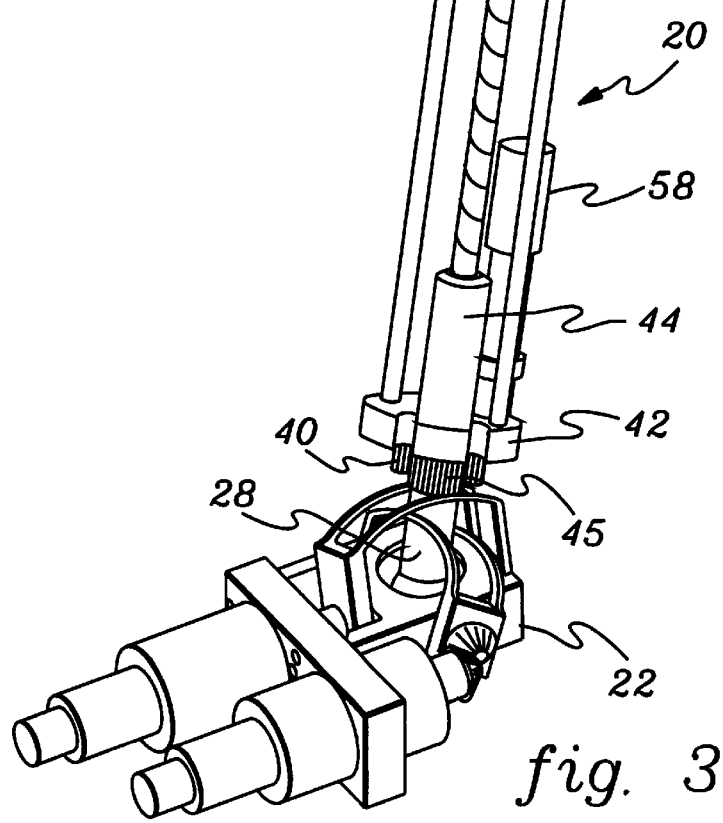
FIG. 3 is a perspective view of the docking station shown in FIGS. 1 and 2.

As shown in FIGS. 3 and 4, exemplary docking station includes a first support 22 which is suitably attachable to stand 12 (FIG. 1) and positionable adjacent to and against an incision in a patient. Support 22 desirably includes an aperture 24 in which is receivable and mountable a spherical member 26 having an aperture therethrough for receiving a hollow tubular sleeve 28.

A pair of arch-shaped members 31 and 32 are attached at their ends to the sides of support 22 for guiding pivotal movement of surgical tool 100 (FIG. 2). Arch-shaped members 31 and 32 each include a slot 33and a slot 34, respectively, which cross each other and through which tubular sleeve 28 extends. A pair of motors 36 and 37 are fixedly attached to support 22 via a plate 23. A gear 38 attached to a rotor of motor 36engages a gear 39 attached to arch-shaped member 31 to selectively pivot surgical tool 100 (FIG. 2) about an X-axis (FIG. 2). In a similar fashion, a gear (not shown) attached to a rotor of motor 37 engages a gear (not shown) attached to arch-shaped member 32 to selectively pivot surgical tool 100 about a Y-axis (FIG. 2). A collar 35having a generally square-shaped outer surface is attached to tubular member 28. The square-shaped outer surface of tubular member 28 matingly engages the sides of slots 33 and 34 to inhibit tubular member 28 from rotating relative to support 22.

With reference to FIG. 3, a gear 40 is fixedly attached to the upper portion of tubular member 28 (FIG. 4) above collar 35 (FIG. 4) and a disk-shaped second support 42 is rotatably attached to tubular member 28 above gear 40 for rotational movement of surgical tool 100 (FIG. 2). A gear 45 attached to a rotor of a motor 44 matingly engages gear 40 to rotate support 42 about a Z-axis (FIG. 2) relative to support 22.

Two elongated rods 50 and 52, and an elongated lead screw 54, each attached at one end to support 42 and extend outward therefrom and attach at opposite ends to an L-shaped member 56 for guiding translational movement of surgical tool 100 (FIG. 2). Disposed between support 42 and L-shaped member 56 is a third support plate 62 having a pair of apertures which slidably engage elongated rods 50 and 52. A third threaded aperture in support 62 matingly engages lead screw 54. A motor 58 is operably connected to lead screw 54 so that rotation of motor 58 causes lead screw 54 to turn, which lead screw 54 in turn, causes support 62 to travel up and down along the Z-axis (FIG. 2).

The attachment of the means for rotating and translating to the means for pivoting provides a compactly configured docking system. Advantageously, such a configuration provides a mechanical system for guiding, constraining or controlling the movement of the releasably attachable and interchangeable surgical tools.

From the present description, it will be appreciated that the motors can be energized via controller 80 to provide a minimum biasing force to maintain a relatively fixed position of the surgical tool in the patient. This allows the surgeon to temporarily remove his hands from the surgical tools, e.g., to adjust the position of endoscope 90, or to replace or change one surgical tool for a second surgical tool having different capabilities or functions. Such a docking station also allows the ready positioning, and in particular, the ready positioning of end effector of the second surgical tool in the patient.

The intersection of the X-axis, the Y-axis, and the Z-axis remains constant and adjacent to the incision in the patient so that the motion of and surgical tool 100, e.g., roll, pitch, and yaw (rotation about Z, Y, and X axes, respectively) and translation (along the Z-axis) inhibit tearing of the incision during an operative procedure.

From the present description, it will also be appreciated by those skilled in the art that other configurations and mechanisms for docking station, e.g., spherical joints, and pneumatic motors, would be equally suitably for guiding, restraining, and controlling a releasably attachable surgical tool in four degrees of freedom.

Figure 5:
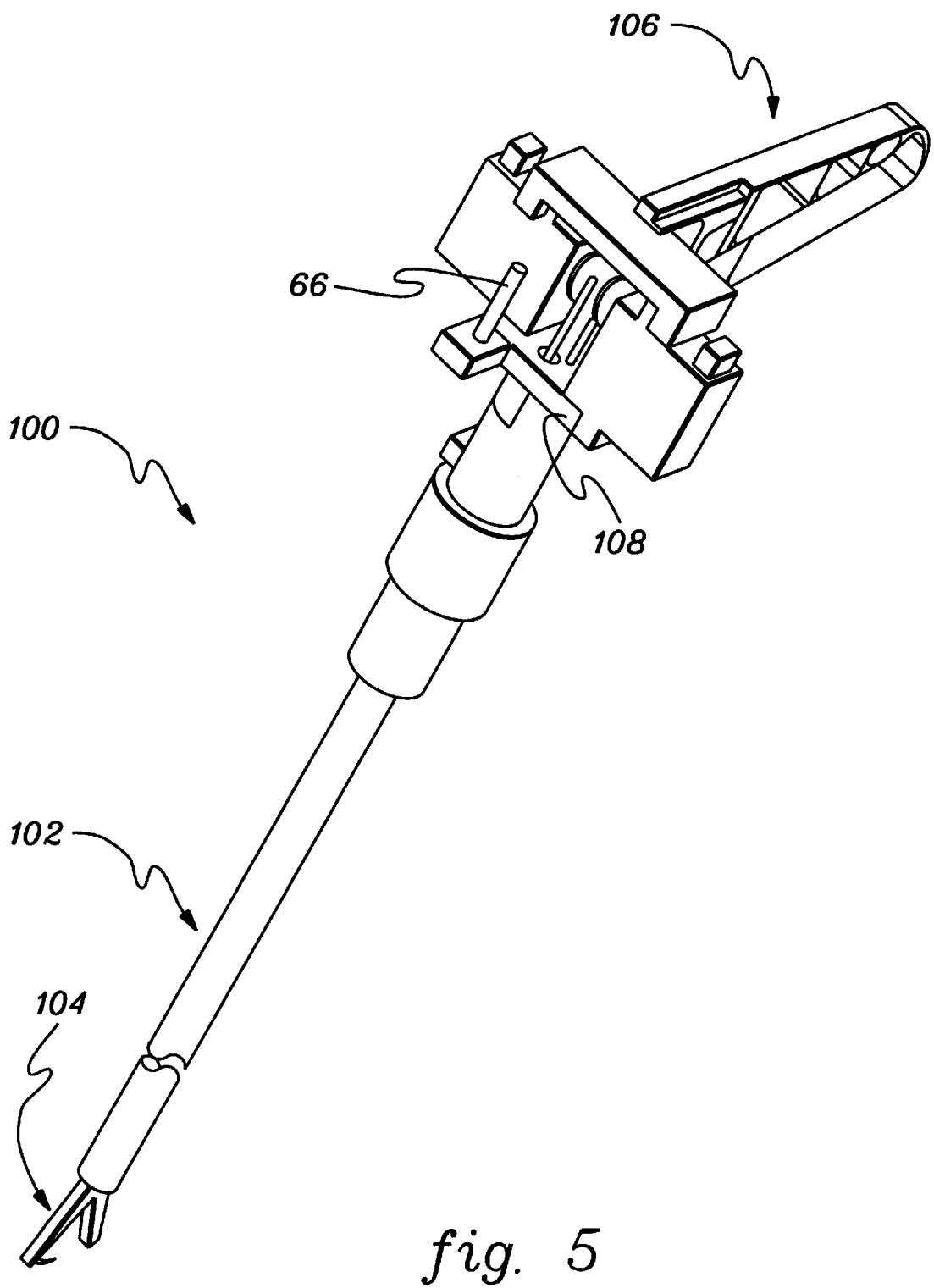
FIG. 5 is an enlarged perspective view of the suturing surgical tool shown in FIGS. 1 and 2.

FIG. 5 illustrates exemplary surgical tool 100 which releasably connects to docking station 20 (FIG. 3) so that a surgeon can easily and quickly disconnect and replace surgical tool 100 with another surgical tool having a different end effector. The exemplary surgical tool 100 includes an elongated body 102 having an end effector 104 at one end and a handle 106 at the other end. Surgical tool 100 desirably includes a plate 108 which releasably attaches to support 62 (FIG. 3) of docking station 20. To connect surgical tool 100 to docking station 20 (FIGS. 1 and 2), handle 106 is passed between elongated rod 50 and lead screw 54 and rotated into place so that elongated body 102 fits within a cutout 64 (FIG. 3) in plate 62 (FIG. 3). End effector 104 is then passed through hollow passageway 29 (FIG. 4) in tubular sleeve 28 (FIG. 4). Support 108 is then releasably connected to support 62 of docking station 20by one or more locking pins 66. Alternatively, support 108 may be suitably connectable to support 62 with one or more screws, or supports 62 and 108 may be suitable provided with snap-fit engaging portions. It will also be appreciated that means may be provided for clampingly engaging supports 62 and 108. Such configurations provide a quick-disconnect for releasably attaching to one or more surgical tools.

Figure 6:
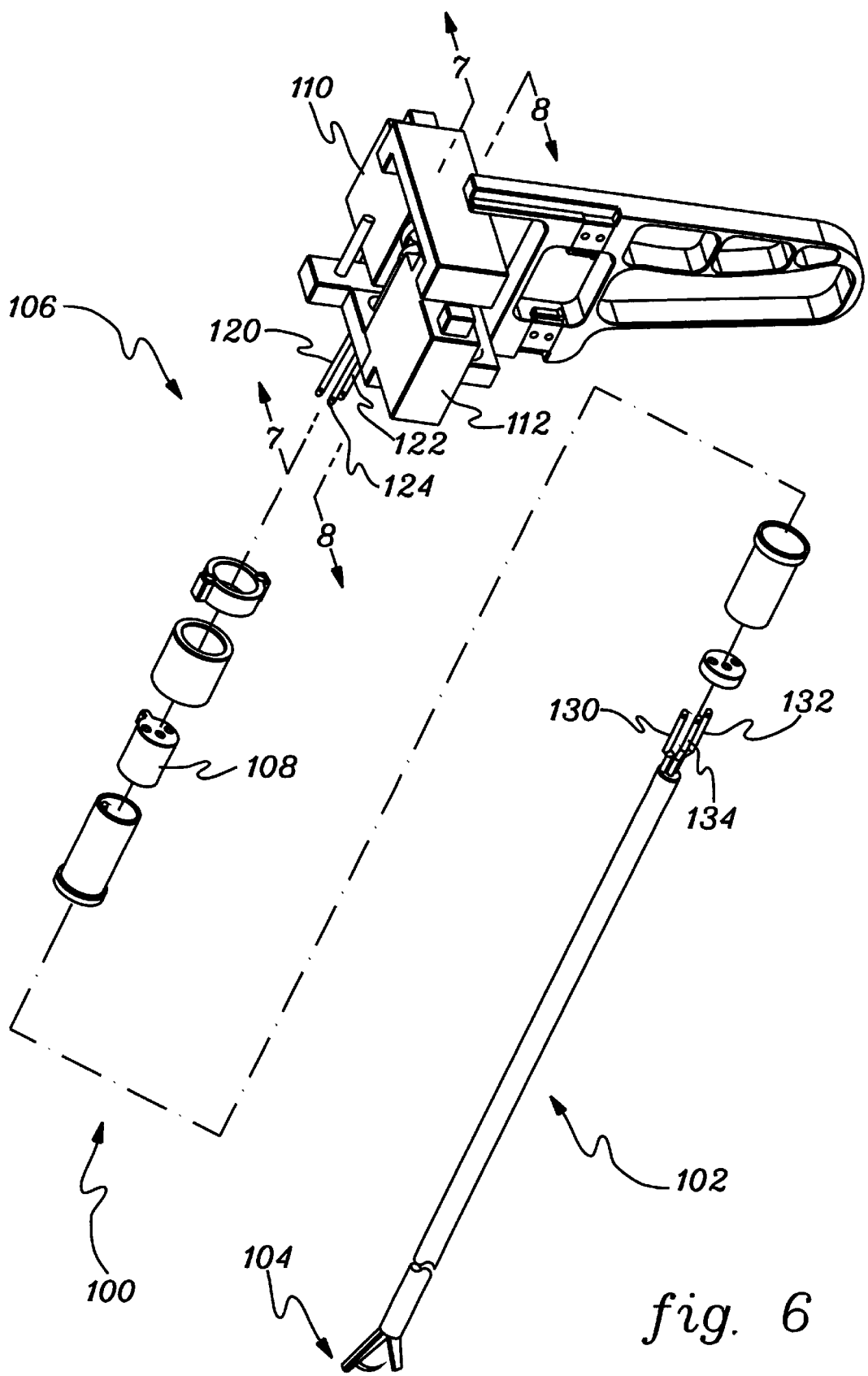
FIG. 6 is an exploded perspective view of the suturing surgical tool shown in FIG. 5.

In a preferred embodiment of surgical tool 100, elongated body 102of surgical tool 100 is desirably releasably attachable from handle 106 as shown in FIG. 6. Desirably elongated bodies of surgical tool are interchangeable as well as disposable after use during an operative procedure on a patient.

Surgical tool 100 provides end effector 104 having a scissor-type motion and, in particular, a suturing tool. In this exemplary embodiment, handle 106 includes two motors 110 and 112 which operably connect to three rods 120, 122, and 124. As shown in FIG. 7, rods 120 and 122 are connected to the ends of a pivoting element 114 which attaches at a center portion to a rotor of motor 110. As the rotor motor 110 rotates back and forth, the control rods 120 and 122 translate along the direction of the Z-axis (FIG. 2) in a reciprocal fashion, i.e., rods 120 and 122 move in opposite directions. As shown in FIG. 8, rod 124 is connected to an end of a pivoting element 116, which attaches to an opposite end to a rotor of motor 112. As the rotor of motor 112 rotates back and forth, rod 124 translates along the direction of the Z-axis in a reciprocal fashion.

The ends of rods 120, 122, and 124 of handle 106 (FIG. 6) are releasably attachable to rods 130, 132, and 134 of elongated body 102 (FIG. 6), as shown in FIG. 9. Each of the end of rods 120, 122, and 124 is hooked-shaped and each of the end of rods 130, 132, and 134 is hooked-shaped so that respective rods (FIG. 6) may be matingly engaged and connected together. After engaging corresponding rods, a coupling ring 108 (FIG. 6) is slid over the intersection of the rods to maintain the rods in an engaged and connected configuration. The motion of rods 120, 122, and 124 is translated to rods 130, 132, and 134 for actuating end effector 104.

Figure 10:
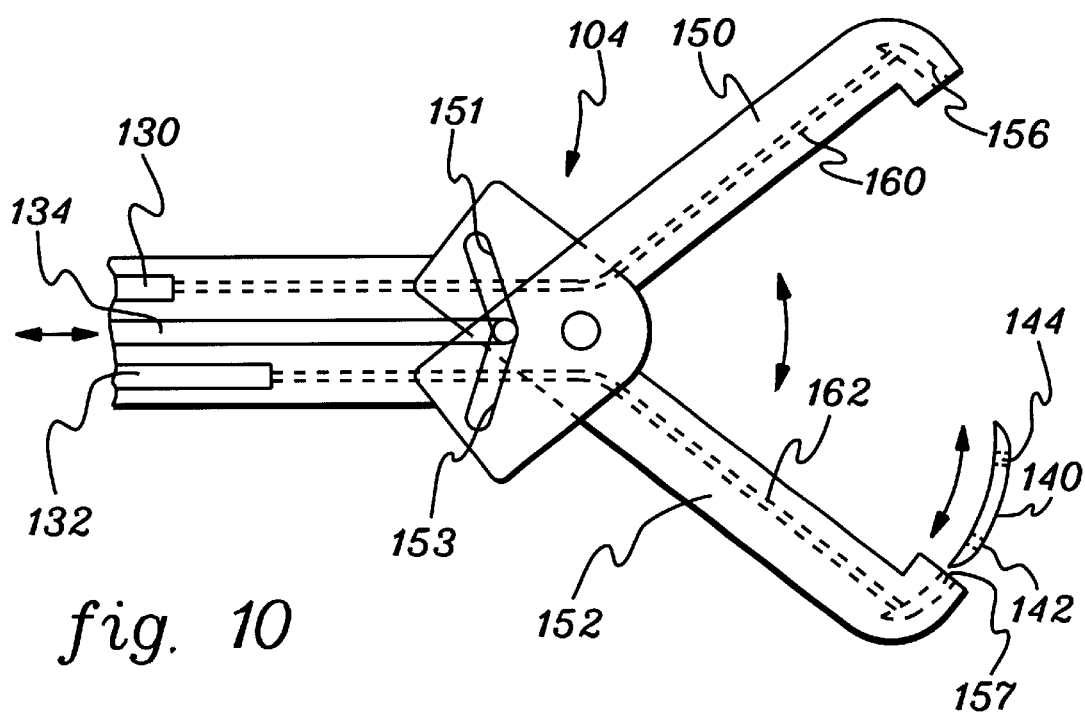
FIG. 10 is an enlarged side elevational view of the suturing end effector shown in FIGS. 5 and 6.

Rods 130, 132, and 134 operably actuate suturing end effector 104 for suturing and, in particular, for passing a needle back and forth from one jaw of suturing end effector 104 to the other jaw. With reference to FIG. 10, actuating scissor-type motion of end effector 104, i.e., opening and closing a jaw 150 and a jaw 152, is effected by rod 134 moving towards and away from end effector 104, via an end portion of rod 134 engaging slots 151 and 153 in the jaws. A needle 140 includes two apertures 142 and 144 which, when rods 130 and 132 move towards and away from end effector 104, flexible cables 160 and 162 attached to rods 130 and 132 engages recesses 156 and 157 in jaws 150 and 152 to lock and unlock needle 140 from jaws 150 and 152.

Figure 11:
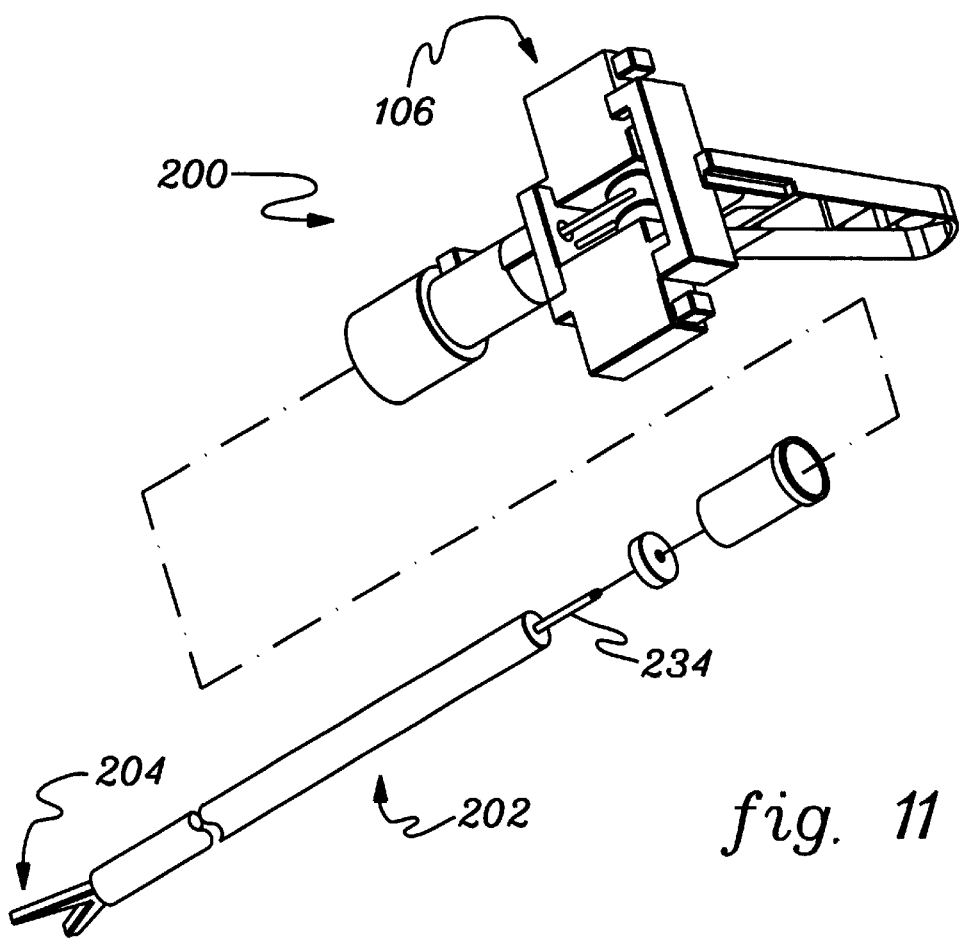
FIG. 11 is an exploded, perspective view of the gripping surgical tool shown in FIG. 1.
Figure 12:
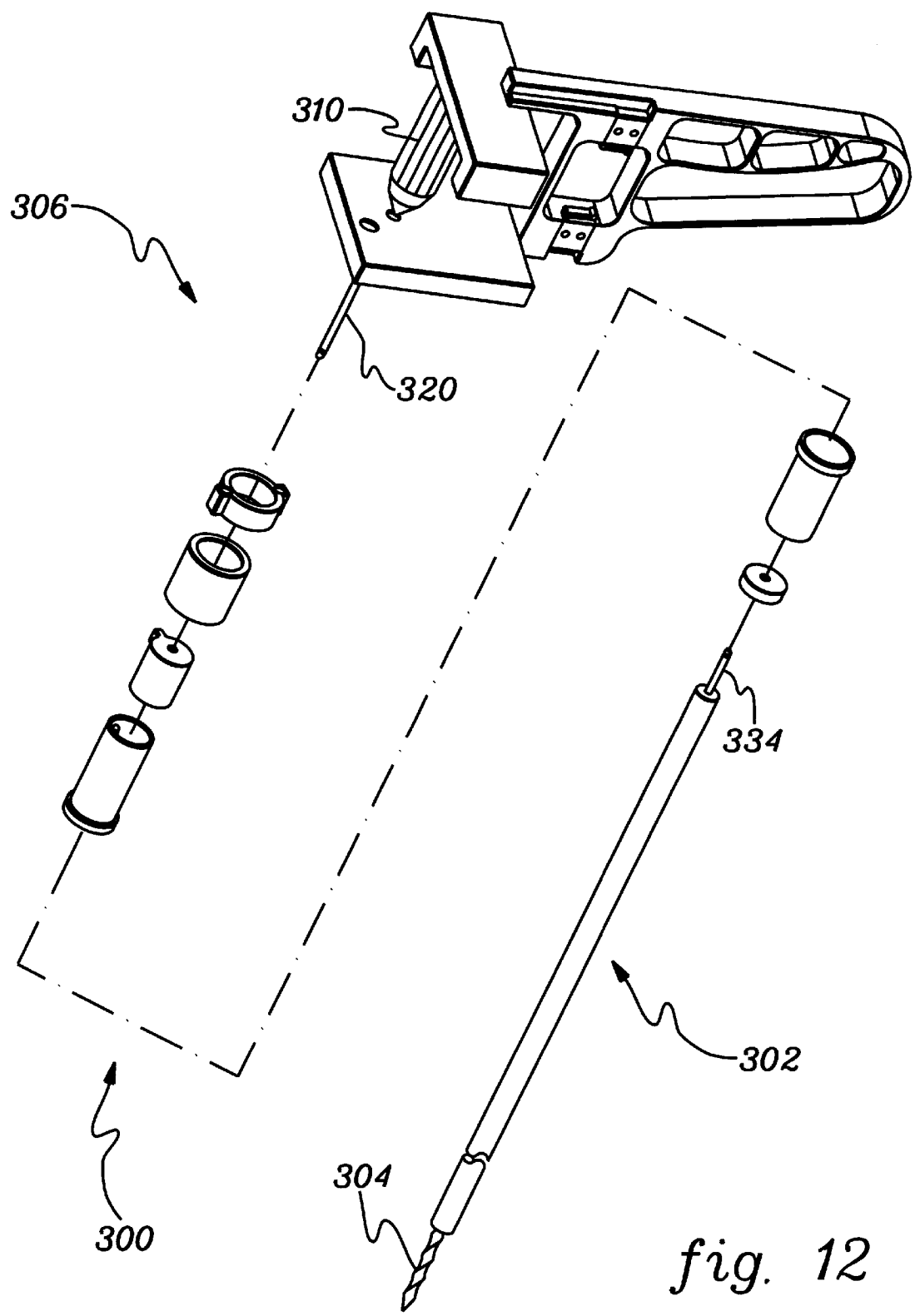
FIG. 12 is an exploded, perspective view of a drilling surgical tool according to the present invention.

FIG. 11 illustrates an alternative embodiment of a gripping surgical tool 200 according to the present invention in which an end effector 204 is operable for grasping items such as suturing threads or needles. In this embodiment, a rod 234 is operably connectable to rod 124 (FIG. 6) of handle 106. FIG. 12 illustrates a surgical tool 300 for performing rotary-type operations (e.g., drilling, buffing, reaming, etc.) according to the present invention. In this illustrated embodiment, surgical tool 300 includes a handle 306 having a motor 310 having a rotor shaft 320 operably releasably attachable to a rod 334 of elongated body 302 for transmitting rotary motion to a drill bit 304.

In addition, it will be appreciated from the present description that a system for minimally invasive surgery may comprise a third docking station which is releasably attachable to a surgical tool which includes an endoscope, e.g., which is inserted through the third incision point in the patient. The third docking station would allow the surgeon to position either manually or via a controller the camera or lens of the endoscope. It will also be appreciated that by providing a docking station which is capable of guiding and/or controlling motion of the surgical tool to four degrees of freedom, stands 12 are merely passive and may be inexpensively manufactured and easily and quickly moved and locked in position at the beginning of each operative procedure in supporting docking stations 20 in a fixed position adjacent the incisions in the patient.

With reference again to FIG. 1, a surgeon using system 10 may specify and perform minimally invasive surgery in a manual mode, a collaborative mode, or an autonomous mode.

In the manual mode of operation of system 10, motors 36, 37, 44, and 58 (FIG. 2) of each of docking stations 20 are desirably back-drivable and are not energized. This allows the surgeon to manually pivotally, rotationally, and translationly move surgical tool 100 via handle 106. Suitable control buttons on handle 106 for controlling motors 110 and 112 allow the surgeon to actuate end effector 104.

The manual mode of operation of system 10 is useful in that the manual mode allows the surgeon to build confidence in system 10, allows the surgeon to perform delicate operations which have not been programmed into controller 80, allows the surgeon to "teach" controller 80 new procedures (e.g., by coding docking station and surgical tool motion under the surgeon's command into the control computer memory), allows the surgeon to use system 10 as an input device, e.g., pointing out a starting and an end point for procedures such as suturing or cutting, locating the starting point and motion vector for drilling, or indicating the location for tying a knot in a suture thread. For teaching controller 80 new procedures or using system 10 as an input device, desirably docking station 20 includes one or more angular sensing devices, e.g., optical encoders which remain active (continuously providing measurements to the controller) during the manual operation as well as during collaborative or autonomous operation.

For example, an optical encoder may consist of a slotted code wheel and an optical transmitter and a receiver. The code wheel is attached to the shaft of the motor. As the motor rotates, the code wheel passes through the transmitter/receiver pair, generating electrical pulses. Counting the pulses produces the angular displacement measurement. Desirably, an optical encoder may be integrated with the motor to reduce the overall packaging size. Suitable miniature motors with optical encoders are available from Micro Mo Electronics of Clearwater, Fla. model numbers 2342S, 1319, etc. Other angular measurement devices may also be used, including a potentiometer and a resolver.

Figure 13:
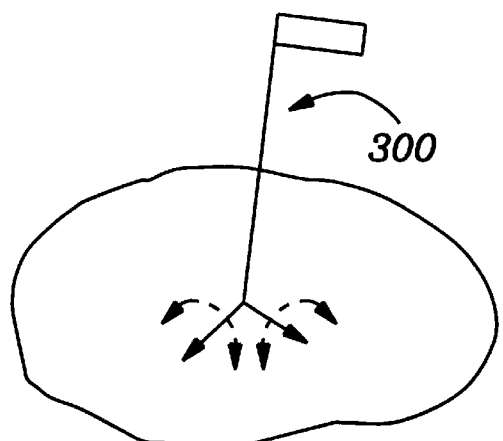
FIG. 13 is diagrammatic illustration of one embodiment of a collaborative control procedure of the docking station shown in FIG. 1.

In the collaborative mode of operating system 10, the system can be collaboratively controlled by both a surgeon and controller 80. This reduces the demand and dexterity required by the surgeon in performing minimally invasive surgery. As shown in FIG. 13, controller 80 may be initialized so that motors 36 and 37 of docking station 20 maintain a fixed orientation along a predetermined axis of translation. For example, the surgeon may then manually move surgical tool 300 having drill bit 304 up and down along the predetermined axis and rotate surgical tool 300 about the predetermined axis while actuating the drill. The computer controlled motions of the surgical tool are illustrated in dashed curved arrows and the manually controlled motions of the surgical tool are illustrated in solid curved arrows in FIG. 13.

Figure 14:
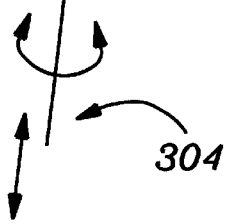
FIG. 14 is diagrammatic illustration of another embodiment of a collaborative control procedure of the docking station shown in FIG. 1.
Figure 14:
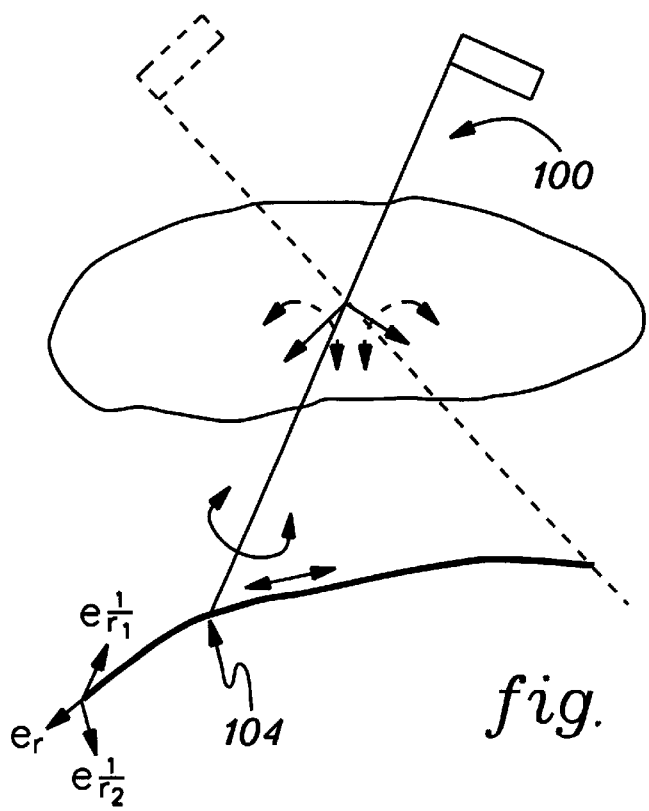

In another example, as shown in FIG. 14, controller 80 may be initialized to control the position of surgical tool 100 along a predetermined three-dimensional path, such as when dissecting tissue or suturing. The surgeon initializes the path, e.g., locates the starting, the intermediate positions, and the ending position, and the computer controls end effector 104 along the path while the surgeon actuates end effector 104 via the handle of surgical tool 100. In such a collaborative operation, the surgical tool may be moved along the path, but the controller will inhibit the surgical tool from deviating from the predetermined path. The computer controlled motions of the surgical tool are illustrated in dashed curved arrows and the manually controlled motions of the surgical tool are illustrated in solid curved arrows in FIG. 13.

The starting, intermediate, and ending positions may also be inputted into controller 80 by the surgeon via a 3D input device such as a 3D mouse connected to controller 80 and monitor 92 to specify the path on a stereo image of the interior of the patient as viewed by a commercially available stereoendoscope.

In the above-noted collaborative controlled cases, suitable computer programs may be developed, as described below, so that controller 80ensures that deviation from a specified path is corrected, but not the motion along the path. Mathematically, as shown in FIGS. 15A and 15B, this means that the surgeon may specify that the end effector position $r_t$ and roll angle $\theta_z$ to be constrained, e.g., $C_t(r_t, \theta_z)=0$.

For the example shown in FIG. 15, the constraint equations can now be written as $$e^T_z V_x = 0 \quad (5)$$

$$e^T_z V_y = 0 \quad (6)$$

where $e_z$ as given below is the tool z-axis
$e_z = R_y R_z R_{z0}$
$R_x = \exp[\theta_x(e_{x0}x)]$
$R_y = \exp[\theta_y((R_x e_{y0})x)]$
and $V_x$ and $V_y$ are unit vectors fixed in the reference frame specifying the plane that the tool Z axis must be perpendicular to.

For the example, shown in FIG. 14, if the tool tip position is restricted to movement along a line with a unit vector $e_r$. If $r_o$ is any vector from the origin of the reference frame to the constraint line, then the constraint relationship is $$(r_t - r_o)^T e^\perp_{r_1} = 0$$
$$(r_t - r_o)^T e^\perp_{r_2} = 0$$

where $$e^\perp_{r_1}$$

and $$e^\perp_{r_2}$$

are any two independent unit vectors perpendicular to $e_r$.

With the forward kinematics (maping from the joint coordinates, $q=(\theta x, \theta y, \theta z, 1)$, the roll-pitch-yaw angles and tool stem translational distance to the end effector coordinate, $(r_t, \theta z)$) can be denoted by $X=k(q)$ (this is known as the forward kinematics). The constraint that the computer needs to enforce is $C_t(k(q))=0$ which can be written more compactly as $C(q)=0$. With the gradient of $C(q)$ written as $J_c(q)$ (the constraint Jacobian matrix, $dC(q)/dq$). During the operation of the system, define $\rho=C(q)$. Then the control algorithm, instead of the usual PID control described above, needs to be modified to $$V=-J^T_c[K_p\rho+K_d\dot\rho+K_i\int^t_o\rho(s)ds]$$

where V is the voltage command to the docking station. The block diagram of above control loop is shown in FIG. 17.

The measured joint angles, $(\theta_x, \theta_y, \theta_z)$, and tool extension 1, are fed into the control computer. The control computer performs the forward kinematics $$r_t=r_1+1R_xR_ye_{z0}$$

to convert the measured quantities to the end effector coordinate $(r_t\theta_z)$. The end effector coordinate is used to compute the constraint variable $_{cr}(r_t, \theta_z)$ (which is maintained as close to zero as possible). The constraint variable goes through a negative feedback (to ensure stability) and PID algorithm to generate a corrective force/torque in the end effector frame. This is converted back to joint motor voltage command by the transpose of the constraint Jacobian, $J_c^T$. The control computer sends this voltage command to the amplifier which in turn drives the motor for the required corrective torque to keep $C_t$ close to zero.

In the autonomous mode of operation of system 10, the controller actively controls one or more docking stations 20 and one or more surgical tools 100. For example, the surgeon may specify an autonomous suturing task with all the intermediate points. As described below, controller 80 may be configured to control suturing surgical tool 100 to puncture a first entry point, exit through a first exit point. Suturing surgical tool 100 may also be controlled to puncture a second entry point, exit through a second exit point. This process can be repeated until the last exit point at which another simple knot will be executed.

In the autonomous mode, to control the tip or end effector of the surgical tool to follow a certain motion profile (position and velocity), controller 80 computes the tracking error based on the encoder measurements and generates a corrective command to the motor. Many control algorithms can be used to achieve this, the discussion here exemplifies only one choice.

For example, the desired tool position $r_{t=(X_t}, Y_t, Z_t)$, in a chosen reference frame (e.g., image frame or some fixed frame in the operating room) and roll angle $\theta_z$ see FIG. 15, can be converted to the joint angles $(\theta_x, \theta_y, \theta_z)$, see FIG. 16, and tool extension 1 which the computer directly controls. This conversion can be computed as follows:

$$L=r_t-r_1$$

$$l=\|L\|$$

where $r_1$ is the (x, y, z) coordinate of the incision point in the reference frame. The tool-z axis at the desired configuration, represented in the reference frame, is given by $$e_z=L/\|L\|$$

When the arch angles, $(\theta_x, \theta_y)$, are zero, call the tool-z axis (in the reference frame) $e_{zo}$. The arch angles can then be computed from standard algorithms from $$e_z=R_yR_xe_{z0}$$

where $$R_x=\exp[\theta_x(e_{xo}x)]$$

$$R_y=\exp[\theta_y((R_xe_{yo})x)]$$

and $e_{xo}$ and $e_{yo}$ are the tool-x and tool-y axes in the zero configuration (configuration at which all angles are defined to be zero), represented in the reference frame.

Figure 18:
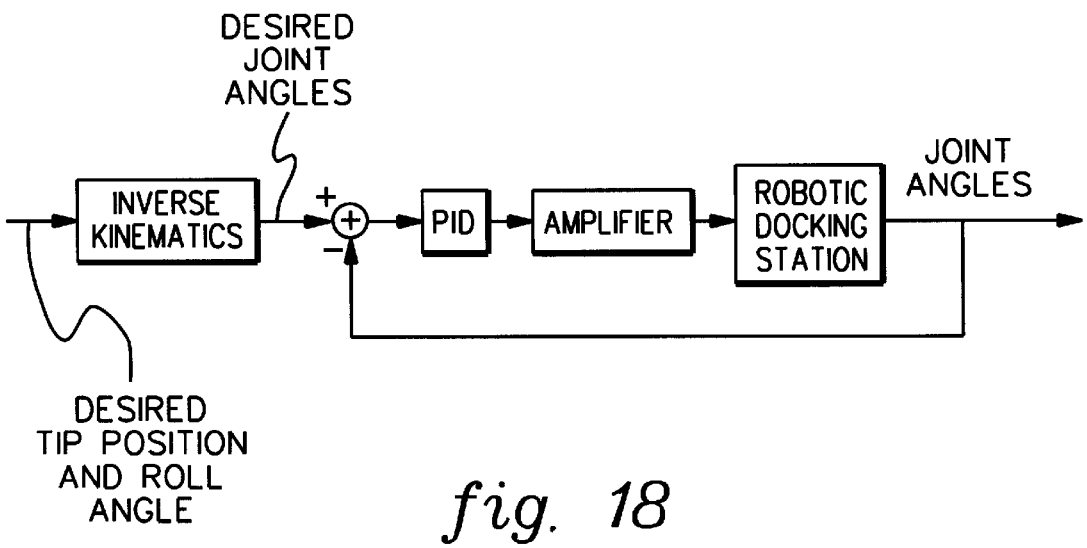
FIG. 18 is a block diagram of an alternative embodiment for collaborative control of the system shown in FIG. 1.

Once this conversion is done, standard proportional—integral-derivative (PID) type of control law may be used for each joint to follow the required path. A block diagram of a control loop for controlling system 10 is shown in FIG. 18.

The difference between the measured and the desired end effector position and roll angle is fed into the PID controller in the control computer. The controller directly generates the joint motor corrective voltage command. The control computer sends this voltage command to the amplifier which in turn drives the motor for the required corrective torque to keep the difference been the desired and actual end effector position and roll angle close to zero.

Suture operations such as tying a knot is a labor intensive procedure which is manually performed by a surgeon. Indeed, as various time-motion studies of endoscopic surgeries have shown, knot tying and suturing are one of the most time consuming procedures.

Another aspect of the present invention system 10 which includes two docking stations 20, one of which is releasably attachable to a surgical tool 20 having a suturing end effector 104, and the other surgical tool 100 having a gripping end effector 204, is configured to incorporate the control procedures described above to autonomously tie a knot in suturing during minimally invasive surgery.

Figure 19:
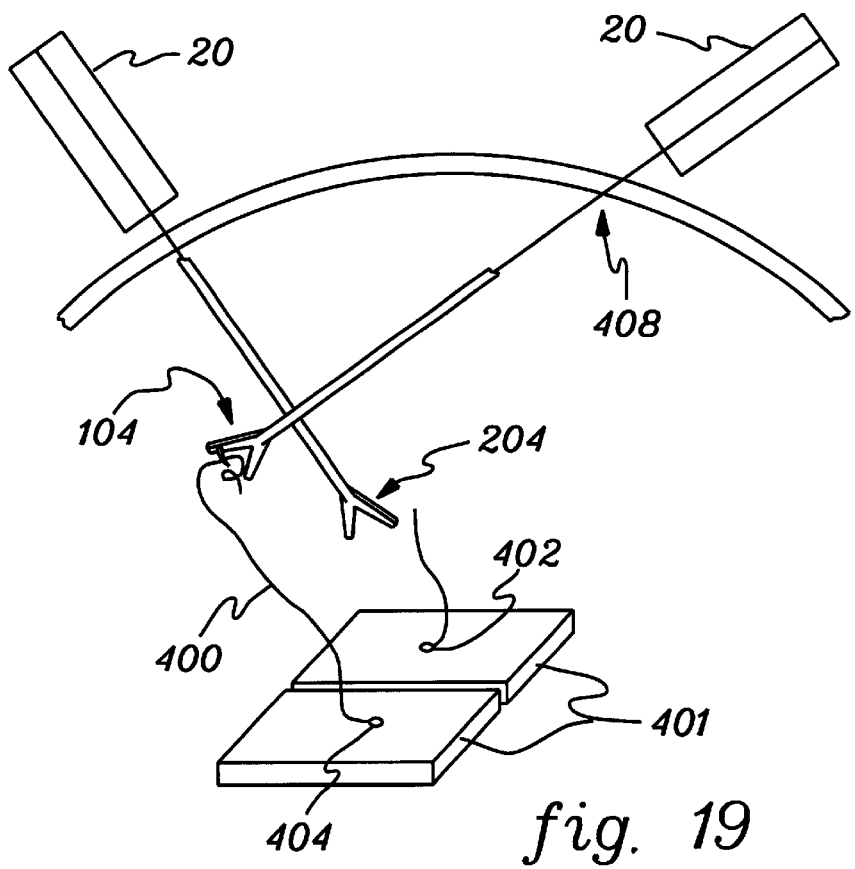
FIG. 19 is a diagrammatic illustration of a setup for a computer implemented method for tying a knot according to the present invention.
Figure 20:
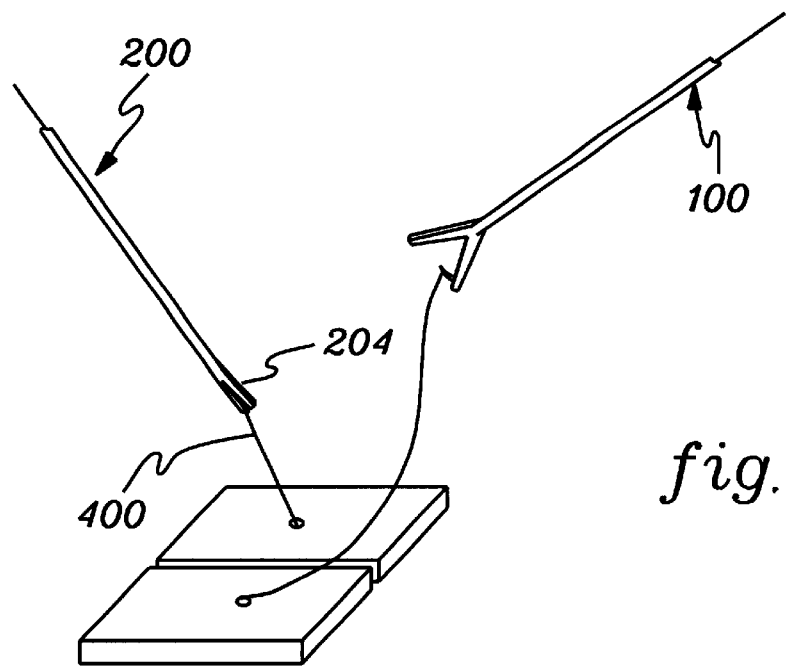
FIGS. 20–27 are diagrammatic illustrations of the steps for tying a knot in suturing according to the present invention.

As shown in FIG. 19, two docking stations 20 are initially positioned above the patient with the end effectors of surgical tools inserted into the patient. A suture thread 400 attached to needle 140 in suturing end effector 104 is inserted into an entry point 402 on the surface of tissue 401 on one side of an incision and exited through an exit point 404 on the surface of tissue 401 on the other side of the incision. This can be done manually by the surgeon or autonomously with the surgeon using the end effector to initialize entry point 402 and exit point 404. As shown in FIG. 20, gripping end effector 204 is used to grasp the tail of suture 400. This may also be done manually by the surgeon or autonomously through an image guided motion via endoscope 90 (FIG. 1).

Controller 80 is operably programmed (e.g., incorporating the motion control procedures with reference to the collaborative control above) to move suturing end effector 104 and gripping end effector 204 to executes the following motions to form a knot as shown in FIGS. 21 through 27. A flowchart of the system for the knot tying procedure is shown in FIG. 28.

Figure 21A:
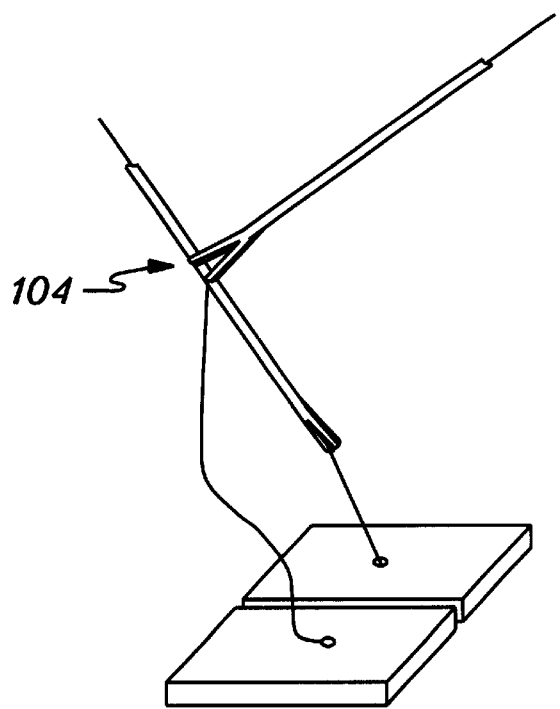
Figure 21B:
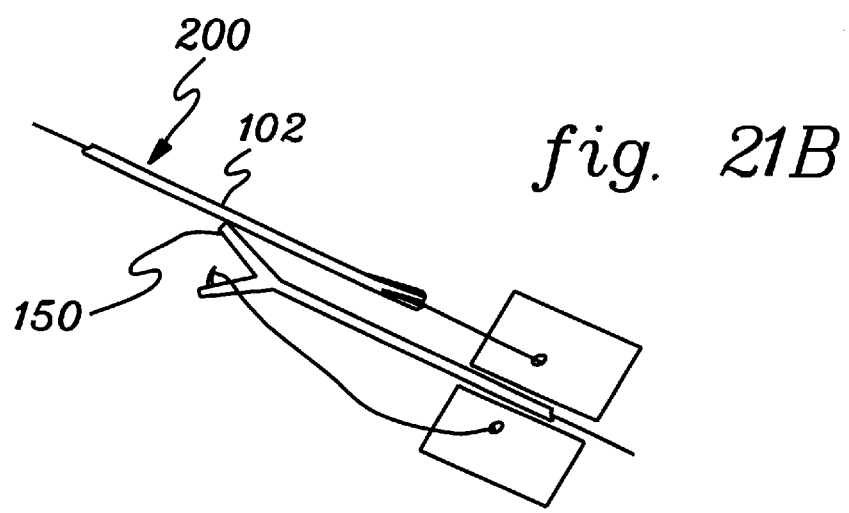
Figure 22A:
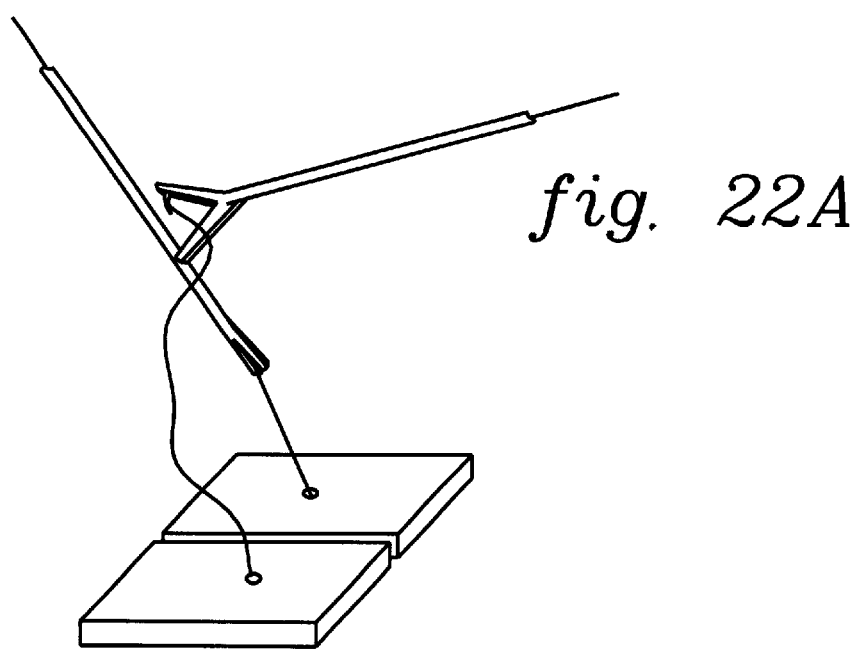
Figure 22B:
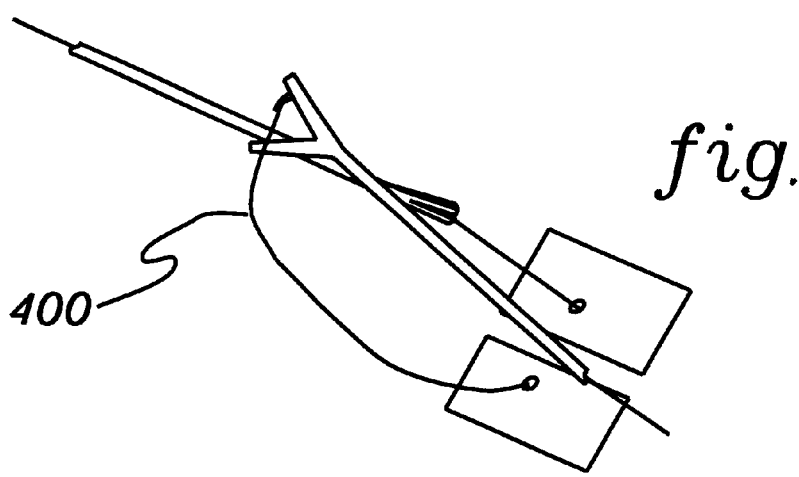

Surgical suturing tool 104 is moved to a position in which jaw 150 (to which needle 140 is not attached) of suturing end effector 104 touches elongated body 102 of gripping surgical tool 200 (FIG. 21 and in particular, FIG. 21B).

Figure 23:
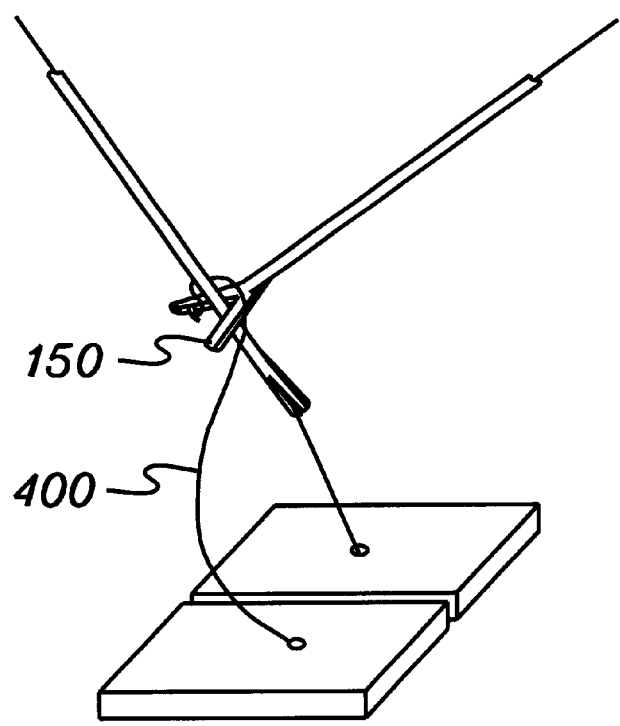

Surgical suturing tool 100 is then rotated (FIGS. 22A and 22B) about a line connecting the point where jaw 150 touches surgical gripping tool 200 and an incision point 408 (FIG. 19) in the patient until the stem of surgical gripping tool 200 is facing the gap between jaw 150 and the tip of needle 140 and so that the suture thread 400 drapes over jaw 150 (FIG. 23).

Figure 24:
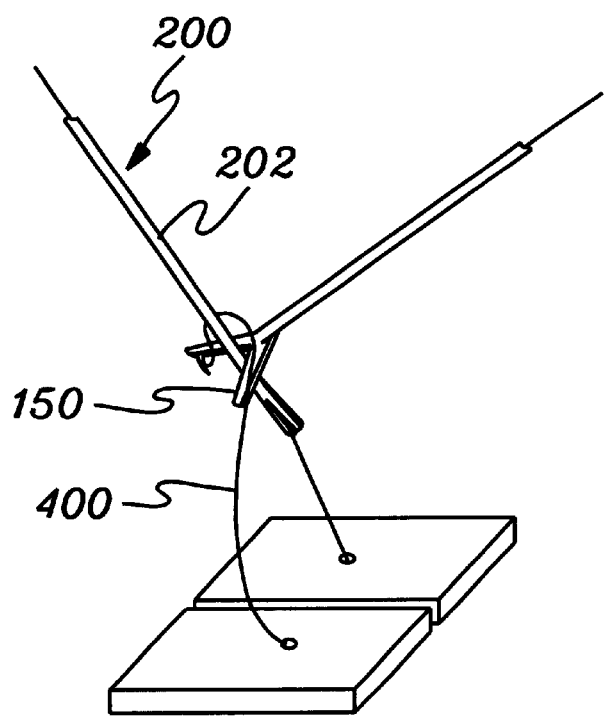
Figure 25:
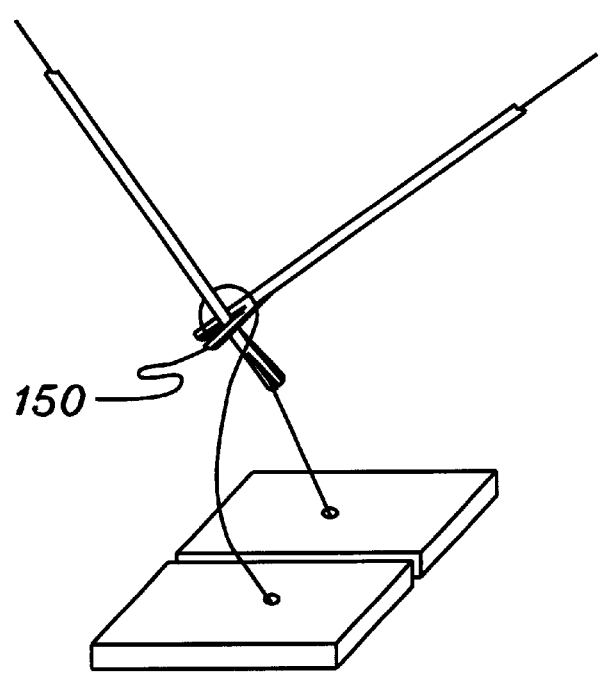

Surgical suturing tool 100 is then moved towards elongated body 202 of gripping surgical tool 200 to ensure that gripping surgical tool 200 is disposed between the jaws and that jaw 150 is ready to receive needle 140 (FIG. 24).

Surgical suturing tool 100 is then actuated to pass needle 140 from jaw 152 to the opposite jaw 150 (FIG. 25), i.e., pass suture thread 140behind gripping surgical tool 200.

Figure 26:
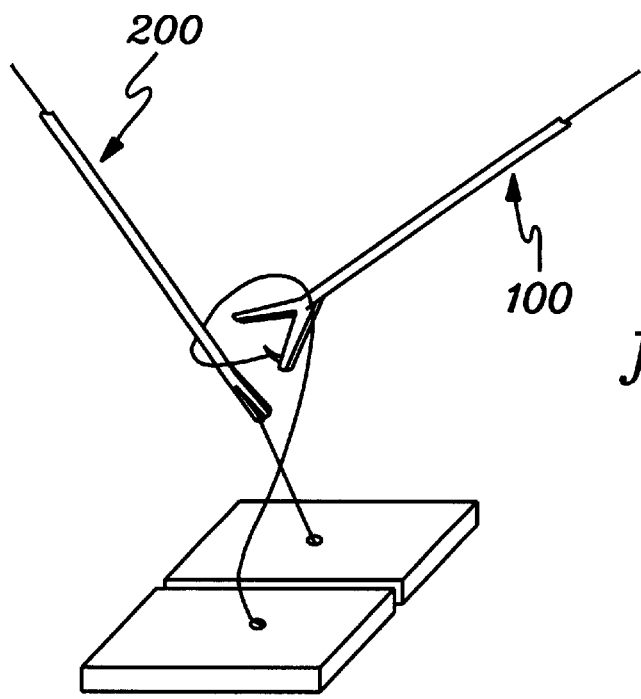
Figure 27:
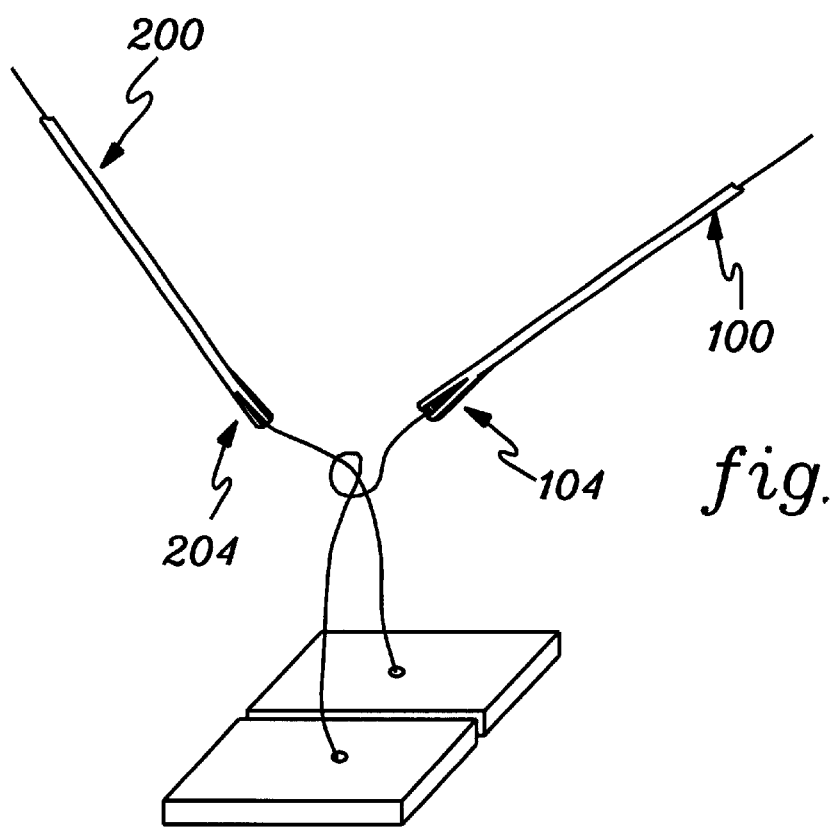
Figure 28:
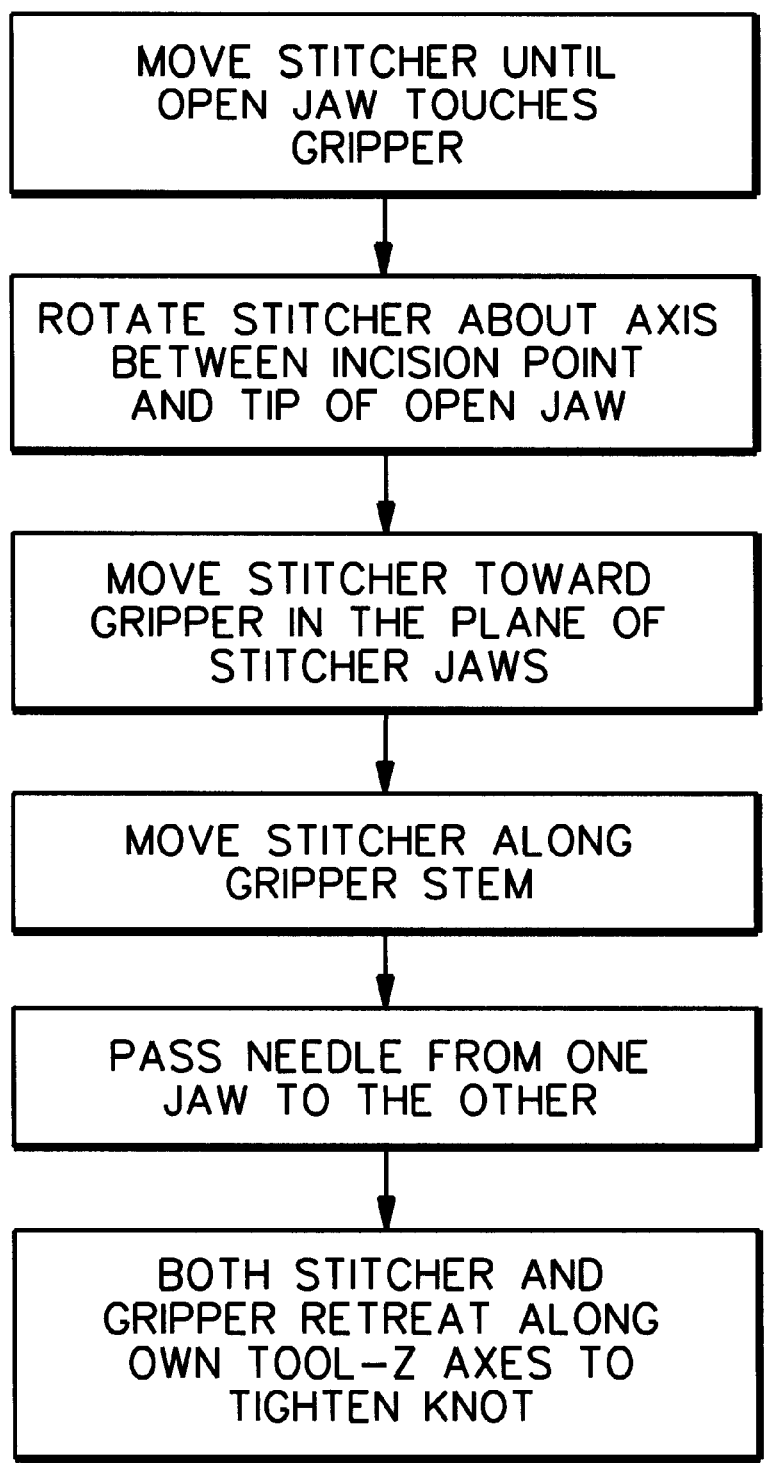
FIG. 28 is a flowchart of the method steps for tying the knot shown in FIGS. 20–27.

Surgical end effector 104 of suturing surgical tool 100 then moves and translates along elongated body 202 of gripping surgical tool 200 so that surgical end effector 104 approaches gripping end effector 204, and both surgical tools are retracted along the Z-axis thereby forming a knot (FIGS. 26 and 27). The process may further be repeated to form a square knot. While the above system is desirably suitable for minimally invasive surgery, it will be appreciated by those skilled in the art that the system may also be used in open surgery.

With reference again to FIG. 1, controller or computing environment 80 incorporating capabilities and techniques of the present invention, in particular the collaborative control and autonomous knot tying, includes, for instance, at least one central processing unit 82, a memory or main storage 84, and one or more input/output devices 86. Desirably, in one example, controller 80 may be provided by a single system environment, e.g., a PENTIUM based computer, or multiple system environment running an operating system. The invention is not limited to such an environment, however, the capabilities of the present invention can be incorporated and used within many types of computer environments and many types of computer systems. Other variations are also possible and are considered a part of the claimed invention.

As is known, central processing unit 82 is the controlling center and provides the sequencing and processing facilities for instruction execution, interruption action, timing functions, initial program loading and other machine related functions. The central processing unit 82 executes at least one operating system, which as known, is used to control the operation of computing processing unit 82by controlling the execution of other programs, controlling communication with peripheral devices and controlling use of the computer resources.

Central processing unit 82 is coupled to main storage 84, which is directly addressable and provides for high speed processing of data by central processing unit 82. Main storage 84 may be either physically integrated with the CPU or constructed in stand alone units.

Main storage 84 is also coupled to one or more input/output devices 86. These devices include, for instance, keyboards, communications controllers, teleprocessing devices, printers, magnetic storage media (e.g., tape cartridges or disks), optical storage media (e.g., CD-ROMs), direct access storage devices, and actuators (e.g., the motors for controlling the motion of the docking station and/or actuation of surgical tools as described above). Data is transferred from main storage 84 to input/output devices 86, and from the input/output devices back to main storage 84.

From the present description, computer readable program code means for implementing the techniques of the present invention for use in computing environment 80, may be readily programmed by those skilled in the art and stored on the above-noted storage media or devices, or imbedded in an integrated circuit.

Although preferred embodiments have been depicted and described in detail herein, it will be apparent by those skilled in the relevant art that various modifications, additions, substitutions and the like can be made without departing from the spirit of the invention and these are therefore considered to be within the scope of the invention as defined in the following claims.

What is claimed is:

1. A compact docking station for use with a stand and a surgical tool in performing minimally invasive surgery through an incision in a patient, said docking station comprising:

means, attachable to the stand and to the surgical tool and positionable generally against the incision in the patient, for restraining movement of the surgical tool to inhibit tearing of the incision in the patient; and means for releasably attaching the surgical tool to said restraining means.

2. The docking station according to claim 1, wherein said restraining means comprises means for pivoting the surgical tool about the incision, means for rotating the surgical tool about an axis through the incision, and means for translating the surgical tool into and out of the incision.

3. The docking station according to claim 2, wherein said means for rotating the surgical tool and said means for translating the surgical tool are operably attached to said means for pivoting the surgical tool.

4. The docking station according to claim 1, wherein said restraining means comprises a spherical member for pivoting the surgical tool about the incision in the patient.

5. The docking station according to claim 1, wherein said restraining means comprises a first support attachable to the stand and a second support for rotation of the surgical tool about an axis through the incision in the patient.

6. The docking station according to claim 5, wherein said restraining means comprises at least one elongated rod attached to said second support for translation of the surgical tool into and out of the incision in the patient.

7. The docking station according to claim 6, wherein said restraining means comprises a third support slidably attachable to said at least one elongated rod and attachable to the surgical tool.

8. The docking station according to claim 6, wherein said at least one elongated rod comprises a lead screw.

9. The docking station according to claim 1, further comprising a plurality of actuators for moving the surgical tool relative to the incision in the patient.

10. The docking station according to claim 9, further comprising a controller for controlling said actuators.

11. The docking station according to claim 10, wherein movement of the surgical tool is selectively moveable by said controller and a surgeon.

12. The docking station according to claim 10, wherein movement of the surgical tool is collaboratively controllable actively by said controller and manually by a surgeon.

13. A compact docking station for use with a stand and a surgical tool in performing minimally invasive surgery through an incision in a patient, said docking station comprising:

a first support attachable to the stand and positionable adjacent to the incision in the patient;

a spherical member pivotally attached to said first support;

a hollow member positioned through said spherical member and having a passageway through which a portion of the surgical tool is slideably receivable and restrained to inhibit tearing of the incision in the patient;

a second support rotatably attached to said hollow member;

at least one elongated bar attached to said second support; and a third support slidably attached to said at least one elongated bar and releasably attachable to the surgical tool.

14. The docking station according to claim 13, further comprising a plurality of actuators for pivoting said spherical member relative to said first support, rotating said second support relative to said first support, and translating said third support relative to said first support.

15. The docking station according to claim 14, further comprising a controller for controlling said actuators.

16. The docking station according to claim 15, wherein movement of the surgical tool is selectively moveable by said controller and a surgeon.

17. The docking station according to claim 15, wherein movement of the surgical tool is collaboratively moveable by said controller and a surgeon.

18. A surgical tool for use in performing minimally invasive surgery through an incision in a patient, said surgical tool releasably attachable to a docking station comprising restraining means, attachable to a stand and the surgical tool and positionable generally against the incision in the patient, for restraining movement of the surgical tool to inhibit tearing of the incision in the patient, said surgical tool comprising;

an elongated body having a first end and a second end;

an end effector attached to said first end of said elongated body;

a handle attached to said second end and manually operable by the surgeon for moving said end effector; and means for releasably attaching said handle to the restraining means of the docking station to restrain movement of said surgical tool to inhibit tearing of the incision in the patient.

19. The surgical tool according to claim 18, wherein said second end of said elongated body is releasably attachable to said handle.

20. The surgical tool according to claim 19, wherein said elongated body and said end effector are disposable.

21. The surgical tool according to claim 18, wherein said handle comprises at least one actuator operably connected to said end effector for actuating said end effector.

22. The surgical tool according to claim 18, wherein said handle comprises means for translating at least one rod through said elongated body for actuating said end effector.

23. The surgical tool according to claim 18, wherein said handle comprises means for translating a plurality of rods through said elongated body for actuating said end effector.

24. The surgical tool according to claim 18, wherein said end effector comprises a scissor-type end effector.

25. The surgical tool according to claim 18, wherein said end effector comprises a rotary-type end effector.

26. The surgical tool according to claim 18, wherein said end effector comprises at least one of a suturing end effector, a grasping end effector, and a drill bit.

27. A system for minimally invasive surgery, said system comprising:

a surgical tool;

a docking station comprising means, attachable to a stand and to said surgical tool and positionable generally against an incision in a patient, for restraining movement of said surgical tool to inhibit tearing of the incision in the patient, said docking station further comprising a plurality of actuators for moving said surgical tool relative to the incision in the patient;

a controller operably connected to said actuators for controlling said actuators; and wherein movement of said surgical tool is collaboratively controllable by said controller and a surgeon.

28. The system according to claim 27, wherein said surgical tool is releasably attachable to said docking station.

29. The system according to claim 27, wherein said surgical tool comprises at least one actuator for actuating an end effector, and said controller is operably connected to said plurality of actuators for actuating said end effector.

30. The system according to claim 27, wherein said docking station comprises a docking station according to claim 13.

31. The system according to claim 30, wherein said surgical tool comprises a surgical tool according to claim 18.

32. A system for tying a knot in minimally invasive surgery, said system comprising:

a first surgical tool comprising a suturing end effector and a first plurality of actuators for actuating said suturing end effector;

a docking station comprising means, attachable to a stand and to said first surgical tool and positionable generally against a first incision in a patient, for restraining movement of said first surgical tool to inhibit tearing of the first incision in the patient, said docking station further comprising a second plurality of actuators for moving said first surgical tool relative to the first incision in the patient;

a second surgical tool comprising a gripping end effector and a third plurality of actuators for actuating said gripping end effector;

a docking station comprising means, attachable to the stand and to said second surgical tool and positionable generally against a second incision in the patient, for restraining movement of said second surgical tool to inhibit tearing of the second incision in the patient, said docking station further comprising a fourth plurality of actuators for moving said second surgical tool relative to the second incision in the patient; and a controller operably connected to said first, second, third, and fourth plurality of actuators for controlling said first, second, third, and fourth plurality of actuators to form a knot in a suturing thread in suturing.

* * * * *